United States Patent
Rovira et al.

(10) Patent No.: US 6,713,753 B1
(45) Date of Patent: Mar. 30, 2004

(54) COMBINATION OF NORMAL AND OBLIQUE INCIDENCE POLARIMETRY FOR THE CHARACTERIZATION OF GRATINGS

(75) Inventors: Pablo I. Rovira, San Francisco, CA (US); Guorong Vera Zhuang, Campbell, CA (US); John D. Heaton, Fremont, CA (US)

(73) Assignee: Nanometrics Incorporated, Milpitas, CA (US)

( * ) Notice: Subject to any disclaimer, the term of this patent is extended or adjusted under 35 U.S.C. 154(b) by 34 days.

(21) Appl. No.: 09/898,641

(22) Filed: Jul. 3, 2001

(51) Int. Cl.$^7$ ............................. G02F 1/01; H01J 40/14
(52) U.S. Cl. ........................................ 250/225; 356/369
(58) Field of Search ................................ 250/225, 334, 250/330, 335.1, 343, 341.3, 559.01, 559.4, 559.49, 559.44–559.45, 559.22, 237 G, 559.09, 203.1, 5, 22, 30; 356/244, 246, 364, 515, 367, 368, 370, 369, 365, 453, 495, 511, 239.3, 239.7, 455, 636

(56) References Cited

U.S. PATENT DOCUMENTS

| | | | |
|---|---|---|---|
| 2,700,918 A | 2/1955 | Osterberg et al. | 88/39 |
| 3,183,763 A | 5/1965 | Koester | 88/14 |
| 3,947,688 A | 3/1976 | Massey | 250/495 |
| 3,992,104 A | 11/1976 | Watanabe | 356/117 |
| 4,105,338 A | 8/1978 | Kuroha | 356/118 |
| 4,141,780 A | 2/1979 | Kleinknecht et al. | 156/626 |
| 4,172,664 A | 10/1979 | Charsky et al. | 356/356 |
| 4,210,401 A | 7/1980 | Batten | 356/369 |
| 4,332,476 A | 6/1982 | Stenberg et al. | 356/369 |
| 4,355,903 A | 10/1982 | Sandercock | 356/382 |
| 4,373,817 A | 2/1983 | Coates | 356/384 |
| 4,408,884 A | 10/1983 | Kleinknecht et al. | 356/355 |
| 4,555,767 A | 11/1985 | Case et al. | 364/563 |
| 4,593,368 A | 6/1986 | Fridge et al. | 364/525 |
| 4,647,207 A | 3/1987 | Bjork et al. | 356/369 |
| 4,672,196 A | 6/1987 | Canino | 250/225 |
| 4,707,610 A | 11/1987 | Lindow et al. | 250/560 |
| 4,748,335 A | 5/1988 | Lindow et al. | 250/572 |

(List continued on next page.)

FOREIGN PATENT DOCUMENTS

| | | | | |
|---|---|---|---|---|
| EP | 0 402 191 A1 | 12/1990 | | G01B/11/02 |
| EP | 0 402 191 B1 | 12/1990 | | G01B/11/02 |
| EP | 0 601 580 A1 | 6/1994 | | G01B/11/06 |

(List continued on next page.)

OTHER PUBLICATIONS

Kley, E. et al., "Application of metallic subwavelength gratings for polarization devices" *SPIE* vol. 2863 (1996) pp. 166–174.

Smith, T., "An Automated Scanning Ellipsometer" *Surface Science* 56 (1976) pp. 212–220.

Collins, R., "Automatic rotating element ellipsometers: Calibration, operation, and real–time appliations" *Rev. Sci. Instrum.* 61 (1990) pp. 2029–2062.

(List continued on next page.)

*Primary Examiner*—David Porta
*Assistant Examiner*—Patrick J. Lee
(74) *Attorney, Agent, or Firm*—Silicon Valley Patent Group LLP (57) ABSTRACT

A normal incidence spectroscopic polarimeter is combined with an oblique incidence spectroscopic polarimeter to provide an accurate characterization of complex grating structures, e.g., structures with sloping sidewalls, with notches and with multiple underlying layers. The normal incidence spectroscopic polarimeter includes a polarizing element that is in the path of the normal incidence light beam such that the light beam is transmitted through the polarizing element before reaching the sample and after being reflected off the sample. The two systems may advantageously share a single light source and/or the spectrophotometer.

20 Claims, 4 Drawing Sheets

U.S. PATENT DOCUMENTS

| | | | |
|---|---|---|---|
| 4,750,822 A | 6/1988 | Rosencwaig et al. | 356/445 |
| 4,826,321 A | 5/1989 | Coates et al. | 356/351 |
| 4,838,695 A | 6/1989 | Mansuripur et al. | 356/369 |
| 4,899,055 A | 2/1990 | Adams | 250/372 |
| 4,982,206 A | 1/1991 | Kessler et al. | 346/108 |
| 5,002,371 A | 3/1991 | Wright | 350/394 |
| 5,007,708 A | 4/1991 | Gaylord et al. | 350/162.2 |
| 5,035,770 A | 7/1991 | Braun | 156/643 |
| 5,042,949 A | 8/1991 | Greenberg et al. | 356/345 |
| 5,042,951 A | 8/1991 | Gold et al. | 356/369 |
| 5,045,704 A | 9/1991 | Coates | 250/372 |
| 5,113,279 A | 5/1992 | Hanamoto et al. | 359/196 |
| 5,155,623 A | 10/1992 | Miller et al. | 359/495 |
| 5,164,790 A | 11/1992 | McNeil et al. | 356/355 |
| 5,179,462 A | 1/1993 | Kageyama et al. | 359/204 |
| 5,191,200 A * | 3/1993 | van der Werf et al. | 250/201.4 |
| 5,191,216 A | 3/1993 | Henderson et al. | 257/28 |
| 5,216,680 A | 6/1993 | Magnusson et al. | 372/20 |
| 5,296,958 A | 3/1994 | Roddy et al. | 359/204 |
| 5,329,357 A | 7/1994 | Bernoux et al. | 356/369 |
| 5,337,146 A | 8/1994 | Azzam | 356/367 |
| 5,349,440 A | 9/1994 | DeGroot | 356/349 |
| RE34,783 E | 11/1994 | Coates | 250/372 |
| 5,363,171 A | 11/1994 | Mack | 355/68 |
| 5,373,359 A | 12/1994 | Woollam et al. | 356/328 |
| 5,406,371 A | 4/1995 | Sakai et al. | 356/367 |
| 5,412,473 A | 5/1995 | Rosencwaig et al. | 356/351 |
| 5,452,091 A | 9/1995 | Johnson | 356/445 |
| 5,504,582 A | 4/1996 | Johs et al. | 356/369 |
| 5,521,706 A | 5/1996 | Green et al. | 356/369 |
| 5,526,117 A | 6/1996 | Wielsch et al. | 356/369 |
| 5,555,474 A | 9/1996 | Ledger | 356/381 |
| 5,596,406 A | 1/1997 | Rosencwaig et al. | 356/327 |
| 5,607,800 A | 3/1997 | Ziger | 430/8 |
| 5,608,526 A | 3/1997 | Piwonka-Corle et al. | 356/369 |
| 5,666,201 A | 9/1997 | Johs et al. | 356/369 |
| 5,706,212 A | 1/1998 | Thompson et al. | 364/525 |
| 5,739,909 A | 4/1998 | Blayo et al. | 356/369 |
| 5,747,813 A | 5/1998 | Norton et al. | 250/372 |
| 5,757,494 A | 5/1998 | Green et al. | 356/369 |
| 5,793,480 A * | 8/1998 | Lacey et al. | 356/73 |
| 5,798,837 A | 8/1998 | Aspnes et al. | 356/369 |
| 5,841,139 A | 11/1998 | Sostek et al. | 250/339.12 |
| 5,867,276 A | 2/1999 | McNeil et al. | 356/445 |
| 5,872,630 A | 2/1999 | Johs et al. | 356/369 |
| 5,877,859 A * | 3/1999 | Aspnes et al. | 356/364 |
| 5,880,838 A | 3/1999 | Marx et al. | 356/351 |
| 5,889,593 A | 3/1999 | Bareket | 356/445 |
| 5,900,633 A | 5/1999 | Solomon et al. | 250/339.08 |
| 5,900,939 A * | 5/1999 | Aspnes et al. | 356/369 |
| 5,910,842 A | 6/1999 | Piwonka-Corle et al. | 356/369 |
| 5,917,594 A | 6/1999 | Norton | 356/327 |
| 5,956,145 A | 9/1999 | Green et al. | 356/364 |
| 5,963,327 A | 10/1999 | He et al. | 356/369 |
| 5,963,329 A | 10/1999 | Conrad et al. | 356/372 |
| 6,031,614 A | 2/2000 | Michaelis et al. | 356/369 |
| 6,097,488 A | 8/2000 | Grek et al. | 356/364 |
| 6,100,985 A | 8/2000 | Scheiner et al. | 356/381 |
| 6,281,974 B1 | 8/2001 | Scheiner et al. | 356/381 |
| 6,366,861 B1 | 4/2002 | Waldhauer et al. | 702/35 |
| 6,384,910 B2 * | 5/2002 | Vaez-Iravani et al. | 356/237.2 |
| 6,429,930 B1 | 8/2002 | Littau et al. | 356/124 |
| 6,429,943 B1 | 8/2002 | Opsal et al. | 356/625 |
| 6,433,878 B1 | 8/2002 | Niu et al. | 356/603 |
| 6,476,920 B1 | 11/2002 | Scheiner et al. | 356/630 |
| 6,483,580 B1 * | 11/2002 | Xu et al. | 356/300 |
| 6,522,406 B1 * | 2/2003 | Rovira et al. | 356/369 |
| 6,556,947 B1 | 4/2003 | Scheiner et al. | 702/172 |
| 6,657,736 B1 | 12/2003 | Finarov et al. | 356/625 |
| 2002/0015146 A1 | 2/2002 | Meeks et al. | 356/73 |
| 2002/0018217 A1 | 2/2002 | Weber-Grabau et al. | 356/601 |
| 2002/0024669 A1 | 2/2002 | Danner et al. | 356/369 |
| 2002/0033945 A1 | 3/2002 | Xu et al. | 356/369 |
| 2002/0033954 A1 | 3/2002 | Niu et al. | 356/601 |
| 2002/0035455 A1 | 3/2002 | Niu et al. | 703/4 |
| 2002/0038196 A1 | 3/2002 | Johnson et al. | 702/179 |
| 2002/0051564 A1 | 5/2002 | Benesh et al. | 382/145 |
| 2002/0105646 A1 | 8/2002 | Zhao et al. | 356/369 |
| 2002/0113966 A1 | 8/2002 | Shchegrov et al. | 356/369 |
| 2002/0149782 A1 | 10/2002 | Raymond | 356/616 |
| 2003/0020912 A1 | 1/2003 | Norton et al. | 356/369 |

FOREIGN PATENT DOCUMENTS

| | | | | |
|---|---|---|---|---|
| EP | 1 037 012 A1 | 9/2000 | | G01B/11/06 |
| JP | 0225038 | 12/1984 | | G01B/11/14 |
| JP | 11-211421 | 8/1999 | | G01B/11/02 |
| JP | 11-211422 | 8/1999 | | G01B/11/02 |
| SU | 1747877 A1 | 7/1992 | | G01B/11/06 |
| WO | WO 99/45340 | 9/1999 | | G11B/11/02 |
| WO | WO 02/25723 A2 | 3/2002 | | H01L/21/66 |
| WO | WO 02/27288 A1 | 4/2002 | | G01J/3/28 |
| WO | WO 02/50501 A1 | 6/2002 | | G01J/4/00 |
| WO | WO 02/079760 A2 | 10/2002 | | G01N/21/21 |

OTHER PUBLICATIONS

Gottesfeld, S. et al., "Combined Ellipsometric And Reflectometric Measurements of Surface Processes on Noble Metal Electrodes" *Surface Science* 56 (1976) pp. 373–391.

Haverlag, M. et al., "In situ ellipsometry and reflectometry during etching of patterned surfaces: Experiments and simulations" *J. Vac. Sci. Technol. B* (1992) pp. 2412–2418.

Johs, B., "Regression calibration method for rotating element ellisometers" *Thin Solid Films* (1993) pp. 395–398.

Azzam, R. et al., "Accurate calibration of the four–detector photopolarimeter with imperfect polarizing optical elements" *Optical Society of America* (1989) pp. 1513–1521.

Azzam, R. et al., "General analysis and optimization of the four–detector photopolarimeter" *J. Opt. Soc. Am. A*, vol. 5 (1988) pp. 681–689.

Azzam, R. "Multichannel polarization state detectors for time–resolved ellipsometry" *Thin Solid Films* (1993) pp. 371–374.

Azzam, R. et al., "Spectrophotopolarimeter based on multiple reflections in a coated dielecric slab" *Thin Solid Films* (1998) pp. 53–57.

Michaelis, A., "Spectroscopic Anisotropy Micro–Ellipsometry (SAME) for determination of lateral and vertical dimensions of sub–micron lithographic structures" *IEEE Catalog No. 99TH8453* (1999) pp. 131–134.

"A Diffraction Grating Analysis Tool", downloaded May 7, 2001 from <http://www.gsolver.com/gsprod.html>, Grating Solve Development Co. (1999).

Ahmed, S., et al., "Comparison of beam propagation method and rigorous coupled–wave analysis for single and multiplexed volume gratings", Applied Optics, vol. 35, No. 22, Aug. 1, 1996, pp. 4426–4435.

Allgair, J. et al., "Implementation of Spectroscopic Critical Dimension (SCDTM) for Gate CD Control and Stepper Characterization", *Proceedings of SPIE*, vol. 4344 (2001), pp. 462–471.

Azzam, R. et al., "Ellipsometry And Polarized Light" *Elsevier Science Publishers* (1977, 1987) pp. 476–481.

Bao, G. et al., "Mathematical studies in rigorous grating theory", *J. Opt. Soc. Am. A*, vol. 12, No. 5 (1995), pp. 1029–1042.

Bao, G. et al., "Modeling and Optimal Design of Diffractive Optical Structures", pp. 1–27. (The correct site is Survey on Industrial Math. 8 (1998), 37–62).

Benson, T. et al., "In–situ Spectroscopic Reflectometry for Polycrystalline Silicon Thin Film Etch Rate Determination During Reactive Ion Etching", Dept. of Electrical Engineering & Computer Science an the Center for Display Technology & Manufacturing, University of Michigan, pp. 1–34.

Bischoff J. et al., "Modeling of optical scatterometry with finite–number–of–periods gratings", *SPIE* vol. 3743 (1999) pp. 41–46.

Bischoff, J. et al., "Single feature metrology by means of light scatter analysis", *SPIE* vol. 3050 (1997) pp. 574–589.

Bishop, K. P. et al., "Grating line shape characterization using scatterometry", *SPIE*, vol. 1545 (1991) pp. 64–73.

Bishop, K. P. et al., "Use of scatterometry for resist process control", *Proc. SPIE—Int. Soc. Opt. Eng.*, vol. 1673 (1992) pp. 441–452.

Bosenberg, W. et al., "Linewidth Measurement on IC Wafers by Diffraction from Grating Test Patterns", *Solid State Technology*, vol. 26, No. 7 (1983) pp. 79–85.

Brauer, R. et al., "Eletromagnetic diffraction analysis of two–dimensional gratings", Optics Communications, vol. 100 (1993) pp. 1–5.

Chang, N. Y., et al., "Algorithm based on rigorous coupled––wave analysis for diffractive optical element design", J. Opt. Soc. Am. A, Opt. Image Sci. Vis. (USA), vol. 18, No. 10, Oct. 2001, pp. 2491–2501.

Chateau, N. et al., "Algorithm for the rigorous coupled––wave analysis of grating diffraction," *J. Opt. Soc. Am. A*, vol. 11 (1994), pp. 1321–1331.

Corle, T., et al., "Polarization–enhanced imaging of photoresist gratings in the real–time scanning optical microscope", *Applied Optics*, vol. 33, No. 4 (1994) pp. 670–677.

Coulombe, S. A. et al., "Modal characteristics of short–pitch photoresist gratings exhibiting zero–order diffraction anomalies", *J. Opt. Soc. Am. A*, vol. 16, No. 12 (Dec. 1999), pp. 2904–2913.

Coulombe, S. A. et al., "Scatterometry measurement of sub–0.1 $\mu$m linewidth gratings", *J. Vac. Sci. Technol.. B*, vol. 16, No. 1 (1998) pp. 80–87.

Coulombe, S. et al., "Ellipsometric–Scatterometry for sub–01. mm CD measurements" *SPIE* vol. 3332 (1988) pp. 282–292.

Damar, H. et al., "Diffraction Characterization for Process Monitoring, Linewidth Measurement and Alignment", *SPIE* vol. 470 (1984) pp. 157–163.

Davidson, M. et al., "A comparison between rigorous light scattering methods", *SPIE* vol. 3051 (1997) pp. 606–619.

Dong Hoon Lee, et al., "Analysis of topological effects of phase–shifting mask by boundary element method", J. Inst. Electron. Eng. Korea D (South Korea), vol. 36–D, No. 11, Nov. 1999, pp. 33–44.

Galarza, C. et al., "Real–time Estimation of Patterned Wafer Parameters Using In Situ Spectroscopic Ellipsometry", *Proceedings of the IEEE* (1999) pp. 773–778.

Gaspar, S. M. et al., "Laser scatterometry for process characterization", *AIP Conference Proceedings*, vol. 227, No. 1, (1991) pp. 54–55.

Gaylord, T. et al., "Analysis and Applications of Optical Diffraction by Gratings," *Proceedings of the IEEE*, vol. 73, (1984), pp. 894–937 (1985).

Glytsis, E. et al., "Rigorous Coupled–Wave Analysis And Applications Of Grating Diffraction", *Critical Reviews Of Optical Science and Technology*, vol. CR49 (1993), pp. 1–31.

Glytsis, E. et al., "Three–dimensional (vector) rigorous coupled–wave analysis of anisotropic grating diffraction", *J. Opt. Soc. Am. A*, vol. 7, No. 8 (1990), pp. 1399–1420.

Glytsis, E. N. et al., "Review of rigorous coupled–wave analysis and of homogeneous effective medium approximations for high spatial–frequency surface–relief", In NASA. Marshall Space Flight Center, Conference on Binary Optics: An Opportunity for Technical Exchange Feb. 23–25, 1993, p 61–76.

Han, Chang–Wook, et al., "Rigorous coupled–wave analysis of antireflective surface–relief gratings" J. Opt. Soc. Korea (South Korea) vol. 1, No. 1, Mar. 1997, pp. 26–35.

Han, S. et al., "Electromagnetic scattering of two–dimensional surface–relief dielectric grating", *Applied Optics*, vol. 31 (1992) pp. 2343–2352.

Hatab, Ziad R. et al., "Sixteen–megabit dynamic random access memory trench depth characterization using two–dimensional diffraction analysis", *J. Vac. Sci. Technol. B*, vol. 13, No. 2 (1995) pp. 174–182.

Hauge, P., "Recent Developments in Instrumentation in Ellipsometry", Surface Science 96, (1980) pp. 108–140.

Haverlag, M. et al., "In situ ellipsometry and reflectometry during etching of patterned surfaces: Experiments and simulations", *Journal of Vacuum Science & Technology B*, vol. 10, No. 6 (1992) pp. 2412–2418.

Heimann, P. et al., "Optical Etch–Rate Monitoring: Computer Simulation of Reflectance", *Journal Electrochem. Soc.*, vol. 131, No. 4 (1984) pp. 881–885.

Henderson, G. N., "Semiconductor quantum electron wave transport, diffraction, and interference: analysis, device, and measurement", Dissertation Georgia Institute Of Technology, vol. 54–10B, 1993, pp. 5312 209 page(s).

Hickman, K. C. et al., "Use of diffracted light from latent images to improve lithography control", *J. Vac. Sci. & Tech. B*, vol. 10, No. 5 (1992) pp. 2259–2266.

Huang, H. et al., "Normal–incidence spectrscopic ellipsometry for critical dimension monitoring", *Applied Physics Letters*, vol. 78 (2001) pp. 3983–3985.

Jarem, J. M., "Rigorous coupled wave analysis of radially and azimuthally–inhom– ogeneous, elliptical, cylindrical systems" (Abstract), J. Electromagn. Waves Appl. (Netherlands), vol. 15, No. 10, 2001, pp. 1367–1368.

Jarem, J. M., et al., "Rigorous coupled–wave analysis of photorefractive reflection gratings", J. Opt. Soc. Am. B, Opt. Phys. (USA) vol. 15, No. 7, Jul. 1998, pp. 2099–2106.

Jarem, J.M. "A rigorous coupled–wave analysis and crossed–diffraction grating analysis of radiation and scattering from three–dimensional inhomogeneous objects" IEEE Transactions on Antennas and Propagation, vol. 46, No. 5, May 1998, p. 740, 741.

Jiang Yongyuan, et al., Rigorous coupled wave analysis of dynamic diffraction properties of photorefractive phase grating Acta Photonica Sin. (China) vol. 29, No. 3, Mar. 2000, pp. 216–222.

Jiang Yongyuan, et al., "Rigorous coupled wave analysis of dynamic property of photorefractive anisotropic self–diffraction" Acta Photonica Sin. (China), vol. 29, No. 9, Sep. 2000, pp. 787–790.

Kamiya, N., "Rigorous coupled–wave analysis for practical planar dielectric gratings. 2. Diffraction by a surface–eroded hologram layer" Appl. Opt. (USA) vol. 37, No. 25, Sep. 1, 1998, pp. 5854–5863.

Kamiya, N., "Rigorous coupled–wave analysis for practical planar dielectric gratings. 3. Increase of higher–order lights owing to degenerated complex diffraction" Appl. Opt. (USA), vol. 37, No. 25, Sep. 1, 1998, pp. 5864–5878.

Kamiya, N., "Rigorous coupled–wave analysis for practical planar dielectric gratings. I. Thickness–changed holograms and some characteristics of diffraction efficiency", Appl. Opt. (USA) vol. 37, No. 25, Sep. 1, 1998, pp. 5843–5853.

Kleinknecht, H. et al., "Linewidth measurement of IC masks and wafers by grating test patterns", *Applied Optics*, vol. 19, No. 4 (1980) pp. 525–533.

Kong, W. et al., "A Hybrid Analysis Ellipsometry Data from Patterned Structures" *Characterization and Metrology for ULSI Technology: 2000 International Conference*, pp. 373–377 (2001).

Kong, W. et al., "Analysis of Time–Evolved Spectroscopic Ellipsometry Data from Patterned Structures for Etching Process Monitoring and Control", Dept. of Electrical Engineering and Computer Science, University of Michigan, Four pages.

Kong, W., "Analysis of Spectroscopic Ellipsometry from Patterned Structures for Etching Process Monitoring and Control", Dissertation University of Michigan, 2001, 141 page(s).

Konstastantinos P. et al., "Use of Light Scattering in Characterizing Reactively Ion Etched Profiles", ATT&T Bell Laboratories, Murray Hill, NJ 07974, Page No. and date unavailable; Also cited in NAN007 RX as Giapis, K. et al., "Use of Light Scattering in Characterizing Reactively Ion Etched Profiles", J. Vac. Sci. Technol. A, vol. 9 (1981), pp. 664–668.

Krukar, R. et al., Overlay and Grating Line Shape Metrology Using Optical Scatterometry (unclassifed) DARPA I 1993 Final Report, (Oct. 11, 1993) Thirty–six pages.

Krukar, R. et al., "Reactive ion etching profile and depth characterization using statistical and neural network analysis of light scattering data", *J. Appl. Phys.*, vol. 74, No. 6 (1993) pp. 3698–3706.

Krukar, R. H. et al., "Analyzing simulated and measured optical scatter for semiconductor process verification", *Proc. SPIE—Int. Soc. Opt. Eng.*, vol. 1907 (1993) pp. 238–249.

Krukar, R. H. et al., "Using scattered light modeling for semiconductor critical dimension metrology and calibration", *Proc. SPIE—Int. Soc. Opt. Eng.*, vol. 1926 (1993) pp. 60–71.

Krukar, R. H. et al., "Wafer examination and critical dimension estimation using scattered light" *Proc. SPIE—Int. Soc. Opt. Eng.*, vol. 1661 (1992) pp. 323–332.

Lee, M. et al., "Analysis of Reflectometry and Ellipsometry Data from Patterned Structures", *Characterization and Metrology for ULSI Technology*, (1998) pp. 331–334.

Lee, S. G., et al., "More stable algorithm for rigorous coupled wave analysis applied to topography simulation in opitcal lithography and its numerical implementation", Proc. SPIE—Int. Soc. Opt. Eng. (USA), vol. 2726, 1996, pp. 288–298.

Lochbihler, H. et al., "Characterization of highly conducting wire gratings using an electromagnetic theory of diffraction" *Optics Communications* 100 (1993) pp. 231–239.

Lochbihler, H. et al., "Charactization of x–ray transmission gratings" *Applied Optics*, vol. 31 (1992) pp. 964–971.

Logofatu, P. C. et al. "Identity of the cross–reflection coefficients for symmetric surface–relief gratings", *J. Opt. Soc. Am. A, Opt.* vol. 16 No. 5 (May 1999) pp. 1108–1114.

Logofatu, P. C. et al. "Measurement precision of optical scatterometry", *Proceedings of SPIE*, vol. 4344 (2001), pp. 447–453.

Logofatu, P. C. et al. "Scatterometry: a metrology for subwavelength surface relief gratings", *Proceedings of SPIE*, vol. 4344 (2001), pp. 472–483.

Logofatu, P. C. et al., "Sensitivity analysis of fitting for scatterometry", *Proc. SPIE—Int. Soc. Opt. Eng.*, vol. 3677 (1999) pp. 177–183.

Logofatu, P.C., "Sensitivity–optimized scatterometry", Dissertation The University of New Mexico, vol. 61–11B, 2000, pp. 5942 181 page(s).

Lopez, A. G. "Reformulation of the rigorous coupled–wave analysis (RCWA) equations: Photonic crystals applications" Dissertation, Cornell University, vol. 61–04B, 2000, pp. 2113 136 pages.

Marx, D. et al., "Polarization quadrature measurement of subwavelength diffracting structures", *Applied Optics*, vol. 36, No. 25 (1997), pp. 6434–6440.

McNeil, J. R. "Application of optical scatterometry to microelectronics processing", *Technical Digest. Summaries of Papers Presented at the Conference on Lasers and Electro–Optics.*, vol. 6 (1998) pp. 348–349.

McNeil, J. R. et al., "Scatterometry applied to microelectronics processing", *Solid State Technol.*, vol. 36, No. 3 (1993) pp. 29–30.

McNeil, J. R., et al., "Scatterometry applied to microelectronics processing" *Solid State Technol.* vol. 36, No. 4 (1993) pp. 53–56.

McNeil, J. R., "Instrumentation to Enhance Optical Scatterometry for Semiconductor Metrology Development", Final Rept. Sep. 1, 1993–Feb. 28, 1998, Contract No. F49620–93–1–0512, Defense Technical Information Center (DTIC) order No.– AD–A354–189 (1998) (23 pages).

McNeill, J. et al., "Scatterometry Applied to Microelectronics Processing" *Microlithography World* (1992) pp. 16–22.

Mills, D. et al., "Spectral ellipsometry on patterned wafers," *SPIE*, vol. 2637 (1995) pp. 194–203.

Milner, L. M et a., "Latent image exposure monitor using scatterometry", *SPIE Proceedings*, vol. 1673 (1992), 10 pages.

Milner, L. M. et al., "Lithography process monitor using light diffracted from a latent image", *Proc. SPIE—Int. Soc. Opt. Eng.*, vol. 1926 (1993) pp. 94–105.

Minhas, B. K. et al., "Ellipsometric scatterometry for the metrology of sub–0.1– μm–linewidth structures", *Applied Optics*, vol. 37 No. 22 (Aug., 1998) pp. 5112–5115.

Minhas, B. K. et al., "Towards sub–0.1 mu m CD measurements using scatterometry", *Proc. SPIE—Int. Soc. Opt. Eng.*, vol. 2725 (1996) pp. 729–739.

Moharam, M. et al., "Diffraction analysis of dielectric surface–relief gratings", *J. Opt. Soc. Am.*, vol. 72 (1982) pp. 1385–1392.

Moharam, M. et al., "Diffraction characteristics of photoresist surface–relief gratings" *Applied Optics*, vol. 23 (1984) pp. 3214–3220.

Moharam, M. et al., "Formulation of stable and efficient implementation of the rigorous coupled–wave analysis of binary gratings", *J. Opt. Soc. Am.*, vol. 12 (1995) pp. 1068–1076.

Moharam, M. et al., "Rigorous coupled–wave analysis of planar–grating diffraction", *J. Opt. Soc. Am.*, vol. 71, No. 7 (1981) pp. 811–818.

Moharam, M. et al., "Stable implementation of the rigorous coupled–wave analysis for surface–relief gratings: enhanced transmittance matrix approach", *J. Opt. Soc Am.*, vol. 12 (1995) pp. 1077–1086.

Moharam, M. et al., "Three–dimensional vector coupled–wave analysis of planar–grating diffraction", *J. Opt. Soc. Am.*, vol. 73, No. 9 (1983), pp. 1105–1112.

Moharam, M., "Coupled–Wave Analysis of Two–Dimensional Dielectric Gratings", *SPIE* vol. 883 (1988) pp. 8–11.

Moharam, M.G. et.al, "Rigorous Coupled–Wave Analysis of Grating Diffraction– E–mode polarization and losses", Journal of the Optical Society of America, vol. 73, No. 4, Apr. 83, p451–455.

Moharam, M.G. et.al, "Rigorous coupled–wave analysis of metallic surface–relief gratings" Optical Society of American, Journal, A: Optics and Image Science Optical Society of America, Journal, A: Optics and Image Science, vol. 3, No. 1986, p. 1780–1787.

Murnane, M. R. et al., "Scatterometry for 0.24–0.70 um developed photoresist metrology", *SPIE*, vol. 2439 (1995) pp. 427–436.

Murname, M. R. et al., "Subwavelength photoresist grating metrology using scatterometry", *Proc. SPIE—Int. Soc. Opt. Eng.*, vol. 2532 (1995) pp. 251–261.

Nakagawa, W., et al., "Analysis of near–field effects in artificial dielectric structures using rigorous coupled–wave analysis", Conference Proceedings—Lasers and Electro–Optics Society Annual Meeting–LEOS, vol. 2, 1999, p 495–496.

Nakagawa, W., et al., "Ultrashort pulse propagation in near–field periodic diffractive structures by use of rigorous coupled–wave analysis", J. Opt. Soc. Am. A, Opt. Image Sci. Vis. (USA), vol. 18, No. 5, May 2001, pp. 1072–1081.

Naqvi, S. S. H. et al., "Etch depth estimation of large–period silicon gratings with multivariate calibration of rigorously simulated diffraction profiles", *J. Opt. Soc. Am. A*, vol. 11, No. 9 (1994) pp. 2485–2493.

Naqvi, S. S. H., et al., "Optical scatterometry for process metrology", *Optical metrology; Proceedings of the Conference*, (Jul. 1999) pp. 129–144.

Niu, X., et al., "Specular Spectroscopic Scatterometry", IEEE Transactions on Semiconductor Manufacturing, vol. 14, No. 2, May 2001, pp. 97–111.

Peng, Song , et al., "Efficient and stable implementation of rigorous coupled–wave analysis for surface–relief gratings", Proc. SPIE—Int. Soc. Opt. Eng. (USA), vol. 2532, 1995, pp. 475–480.

Peng, Song, et al., "Efficient implementation of rigorous coupled–wave analysis for surface–relief gratings", Journal of the Optical Society of American A: Optics and Image Science, and Vision, vol. 12, No. 5, May 1995, p 1087–1096.

Press, W. et al., "Numerical Recipes: The Art of Scientific Computing,", *Cambridge University Press*, Section 14.4 (1986), pp. 521–528.

Prins, S. L. et al., "Scatterometric sensor for PEB process control", *Proc. SPIE—Int. Soc. Opt. Eng.*, vol. 2725 (1996) pp. 710–719.

Raymond, C. et al., "Metrology of subwavelength photoresist gratings using optical scatterometry" *J. Vac. Sci. Technololgy.* B 13 (1995) pp. 1484–1495.

Raymond, C. et al., "Resist and etched line profile characterization using scatterometry" *SPIE* vol. 3050 (1977) 476–486.

Raymond, C. et al., "Scatterometry for the measurement of metal features" *Proceedings of SPIE vol. 2998* (2000) pp. 135–146.

Raymond, C. J. et al., "Multiparameter CD measurements using scatterometry", *Proc. SPIE—Int. Soc. Opt. Eng.*, vol. 2725 (1996) pp. 698–709.

Raymond, C. J. et al., "Multiparameter grating metrology using optical scatterometry" *J. of Vac. Sci. Tech. B*, vol. 15, No. 2 (1997) pp. 361–368.

Raymond, C. J. et al., "Multi–parameter process metrology using scatterometry", *Proc. SPIE—Int. Soc. Opt. Eng.*, vol. 2638 (1995) pp. 84–93.

Raymond, C. J. et al., "Resist and Etched line profile characterization using scatterometry", *Proc. SPIE—Int. Soc. Opt. Eng.*, vol. 3050 (1997) pp. 476–486.

Raymond, C. J. et al., "Scatterometry for CD measurements of etched structures", *Proc. SPIE—Int. Soc. Opt. Eng.*, vol. 2725 (1996) pp. 720–728.

Sohail, S. "A simple technique for linewidth measurement of gratings on photomasks", *Proc. SPIE—Int. Soc. Opt. Eng.*, vol. 1261 (1990) pp. 495–504.

Sohail, S. et al. "Grating parameter estimation using scatterometry" *Proc. SPIE—Int.Soc. Opt. Eng.*, vol. 1992 (1993) pp. 170–180.

Sohail, S. et al., "Diffractive techniques for lithographic process monitoring and control",*J. Vac. Sci. Technol. B*, vol. 12, No. 6 (1994) pp. 3600–3606.

Sohail, S. et al., "Linewidth measurement of gratings on photomasks: a simple technique", *Applied Optics*, vol. 31, No. 10 (1992) pp. 1377–1384.

Stover, J. C., et al., "Modeled and measured scatter from vias", SPIE Conf on Surface Characterization of Computer Disks, Wafers, and Flat Panel Displays, Jan. 1999, pp. 65–71.

Sun, J. et al., "Profile Measurement on IC Wafers by Holographic Interference", *SPIE* vol. 673 (1986) pp. 135–143.

Tadros, K., "Understanding metrology of polysilicon gates through reflectance measurements and simulation", *SPIE* vol. 1464 (1991) pp. 177–186.

Tu, K. et al., "Multiple–scattering theory of wave diffraction by superposed volume gratings",*J. Opt. Soc. Am. A.*, vol. 7, No. 8 (1990), pp. 1421–1435.

Wilson, S. M. G. et al., "Phase shift mask metrology using scatterometry", *Proc. SPIE—Int. Soc. Opt. Eng.*, vol. 2322 (1994) pp. 305–315.

Yeung, M., et al., "Electromagnetic Scatterometry Applied to In Situ Metrology", *Proceedings of SPIE*, vol. 4344 (2001), pp. 484–495.

Ziger, D. et al., "Linesize effects on ultraviolet reflectance spectra", *Society of Photo–Optical Instrumentation Engineers* (1997), Paper 37046.

Zylberberg, Z. et al., "Rigorous coupled–wave analysis of pure reflection gratings" Optical Society of America, Journal, vol. 73, Mar. 1983, p. 392–398.

\* cited by examiner

COMBINATION OF NORMAL AND OBLIQUE INCIDENCE POLARIMETRY FOR THE CHARACTERIZATION OF GRATINGS

FIELD OF THE INVENTION

This invention relates in general to metrology devices and in particular to metrology devices that may be used to measure diffracting and anisotropic structures.

BACKGROUND

The reduction on the size of microchip components requires new metrology technologies for monitoring critical dimensions (CDs). Optical metrology techniques are particularly advantageous because they are non-destructive, non-invasive, economical and compact. Certain structures are particularly difficult to accurately measure. For example, complex line profiles, such as sloping sidewalls, undercut sidewalls, and notches in the sidewalls can be difficult to measure accurately.

Thus, what is needed is an optical metrology tool to measure quickly and accurately diffraction gratings, including diffraction gratings having complex cross-sectional profiles.

SUMMARY

A normal incidence polarimeter is combined with an oblique incidence polarimeter, in accordance with an embodiment of the present invention, to provide an accurate characterization of complex grating structures, e.g., structures with sloping sidewalls, notches, and/or multiple underlying layers. In one embodiment, spectroscopic polarimeters are used.

The normal incidence polarimeter includes a polarizing element that is in the path of the normal incidence light beam. The normally incident light passes through the polarizing element before reaching the sample and after being reflected off the sample. The oblique incidence polarimeter includes a polarization stage generator in the light path before the sample and a polarization state detector in the light path after the sample.

The metrology device may use a single light source to produce the normally incident light beam and the obliquely incident light beam. Alternatively, multiple light sources may be used. In addition, the metrology device may use a single spectrophotometer to detect both the obliquely incident light beam and the normally incident light beam after being reflected off the sample. Alternatively, the normal incidence polarimeter and the oblique incidence polarimeter may use separate spectrophotometers.

DETAILED DESCRIPTION

Figure 1:
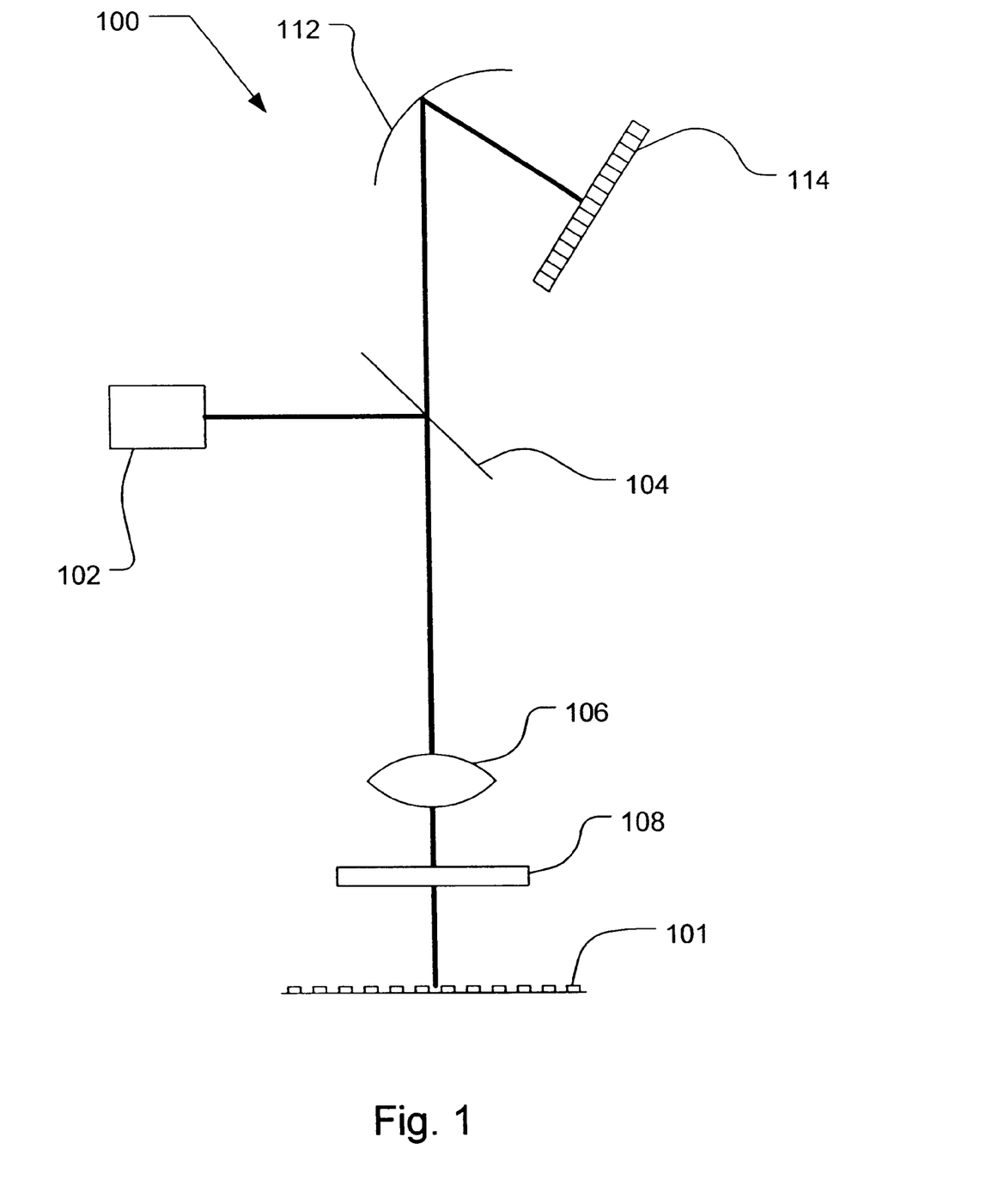
FIG. 1 shows a normal incidence spectroscopic polarimeter that may be used for the characterization of profiles of lines on a grating sample.

FIG. 1 shows a normal incidence spectroscopic polarimeter 100, which acts as a polarized reflectometer that may be used for the characterization of profiles of lines on a grating sample 101. The system shown in FIG. 1 includes a broadband light source 102, a beam splitter 104, which deviates the light beam towards the microscope objective lens 106. The light beam passes through objective lens 106 and is then polarized by a polarizer 108, which is rotatable. The polarized light beam is incident on and reflected by the grating sample 101. The reflected light is again transmitted through the polarizer 108 and the objective lens 106. The light beam passes through the beam splitter 104 and is focused into the slit of a spectrograph 110, which includes, e.g., a diffraction grating 112 and a multichannel array detector 114. Normal incidence spectrocopic polarimeter 100 is described in more detail in U.S. Patent Application entitled "Apparatus And Method For The Measurement Of Diffracting Structures" by J. Holden et al., Ser. No. 09/670,000, filed Sep. 25, 2000, and in U.S. Patent Application entitled "Measurement Of Diffracting Structures Using One-Half Of The Non-Zero Diffracted Orders" by W. McGahan, Ser. No. 09/844,559, filed Apr. 27, 2001, both of which have the same assignee as the present disclosure and both of which are incorporated herein by reference.

One of the advantages of normal incidence polarimetry is the relatively simple calibration and alignment procedures, as well as the ease of integration with microelectronics processing tools. Further, the normal incidence spectroscopic polarimeter 100 can be used to measure reflectance spectra, i.e., $R_{ET}$ and $R_{TM}$, or ellipsometry data, i.e., $\psi$ and $\Delta$. Furthermore, the simulation of reflectance or ellipsometry spectra requires the use of Rigorous Coupled-Wave Analysis calculation, which is time consuming. Due to the symmetry of the normal-incidence configuration, however, the calculation time to generate a modeled spectrum at normal incidence can be orders of magnitude smaller than at oblique incidence. Consequently, normal incidence spectroscopic polarimetry is a useful technique for integrated metrology, where the measurement throughput is one of the most important issues.

Figure 2A:
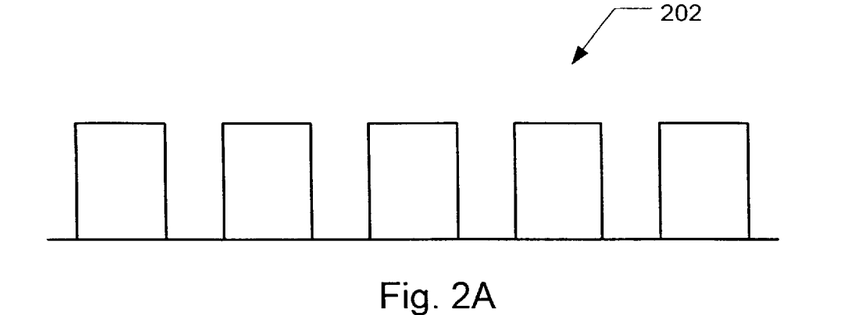
FIGS. 2A to 2D show various line profiles in a diffraction grating.
Figure 2B:
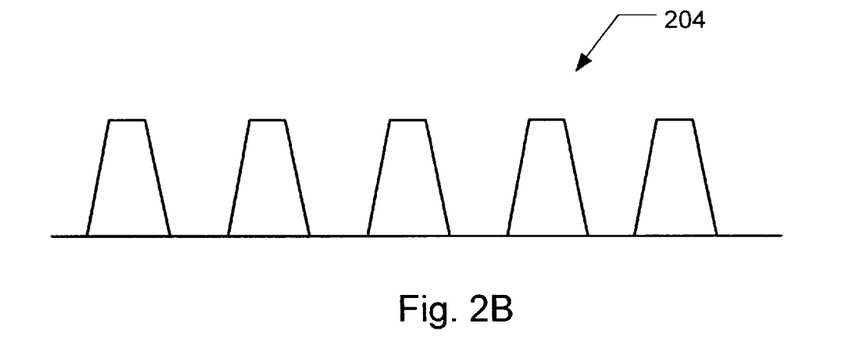
Figure 2C:
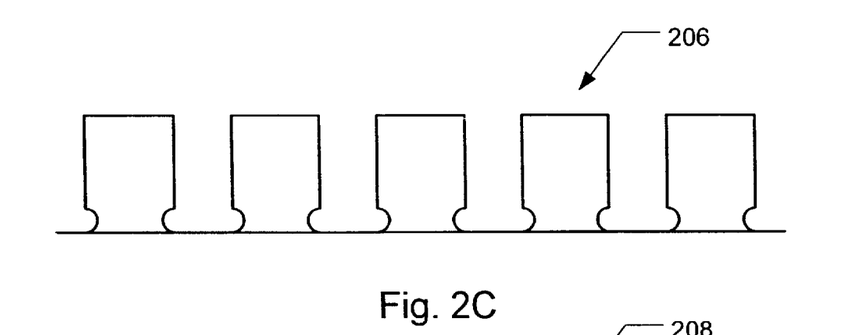
Figure 2D:
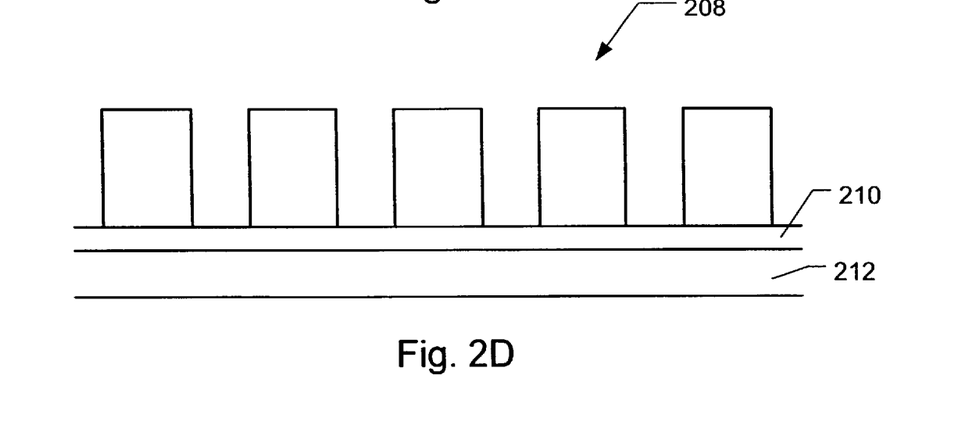

As shown in FIG. 2A, line profiles are often approximated as rectangular grating 202, e.g., with horizontal sidewalls. However, line profiles can become more complicated, as shown in FIGS. 2B, 2C and 2D. FIG. 2B shows a trapezoid grating 204 having sloped sidewalls. FIG. 2C shows a notched grating 206 with horizontal sidewalls with a groove at the base of each line. FIG. 2D shows a rectangular grating 208 with a stack of films 210, 212 underneath the grating 208. Of course, many other complicated structures may exist, including combinations of the structures shown in FIGS. 2B, 2C, and 2D.

For complicated structures, such as those shown in FIGS. 2B, 2C, or 2D, it may be desirable to provide more data related to the structure than can be provided by normal incidence polarimeter 100 in order to accurately analyze the total structure.

Figure 3:
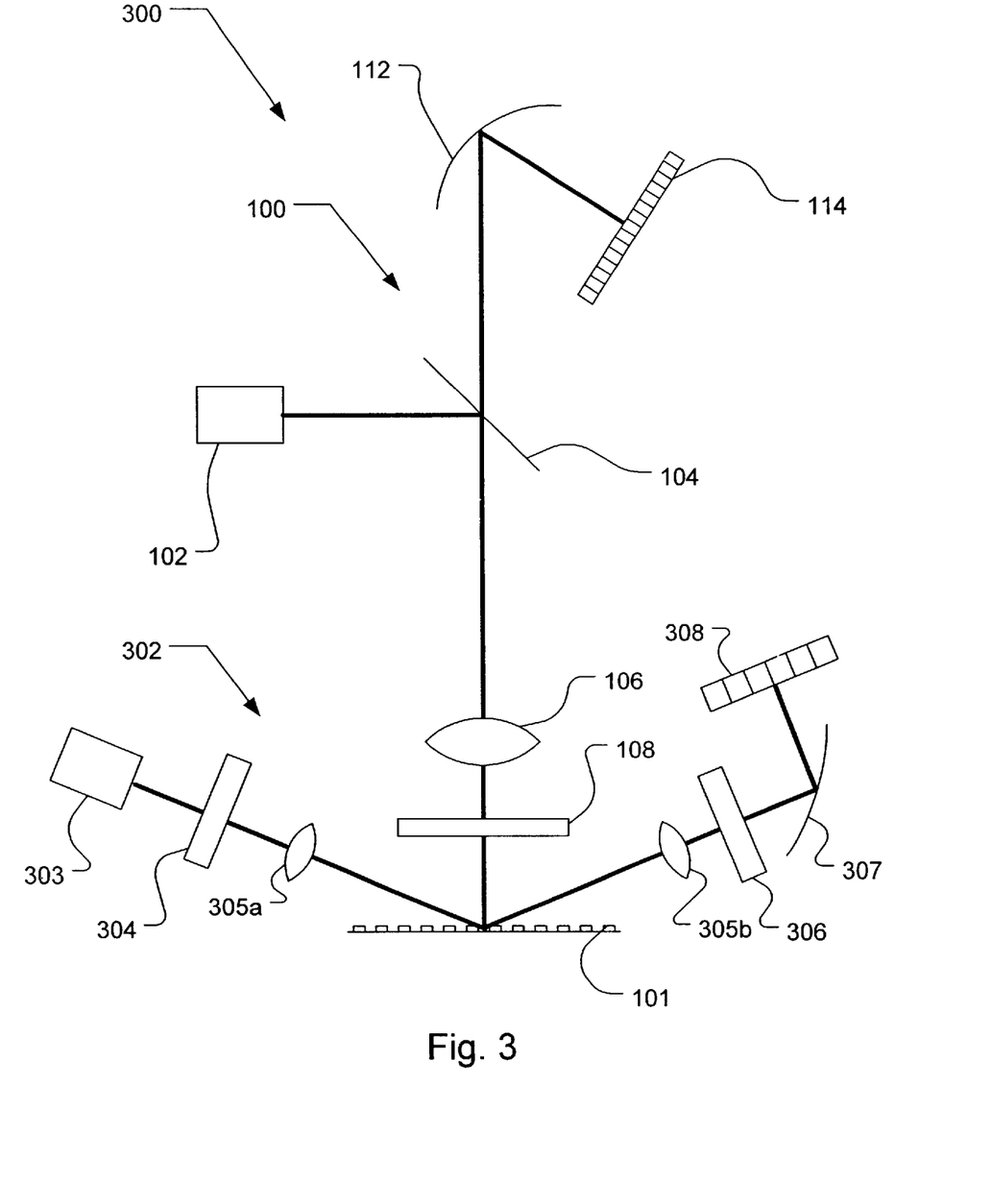
FIG. 3 shows a combined metrology system that includes a normal incidence spectroscopic polarized reflectometer and an oblique incidence polarimeter.

FIG. 3 shows a combined metrology system 300 that includes a normal incidence spectroscopic polarimeter 100 and an oblique incidence polarimeter 302. It should be understood that if desired, polarimeters 100 and 302 may use a single wavelength of light. The normal incidence spectroscopic polarimeter 100 operates as described above. The oblique incidence polarimeter 302 includes a light source 303 and a polarization state generator (PSG) 304, a lens 305a (or series of lenses) before the sample 101, another lens 305b (or series of lenses) after the sample 101, a polarization state detector (PSD) 306, a diffraction grating 307 and a multichannel array detector 308, which analyze the polarization state after reflection, from which the ellipsometry angles (ψ, Δ) can be obtained. The PSG 304, e.g., can be a linear polarizer with its transmission axis at an angle from the plane if incidence, whereas the PSD 306 may consist on either a rotating compensator and fixed analyzer, a rotating analyzer, a photoelastic modulator followed by an analyzer, or anything else that creates an intensity modulation as a function of a known system parameter such as position of the compensator fast axis or analyzer transmission axis in the case of a rotating compensator or rotating analyzer system, respectively, or effective phase retardance as a function of time in case of a photoelastic modulator. The ellipsometry angles (ψ, Δ) can then be extracted from the mathematical analysis of the modulated intensity using Jones matrix or Muller matrix formalisms, as can be understood by someone skilled in the art.

Figure 4:
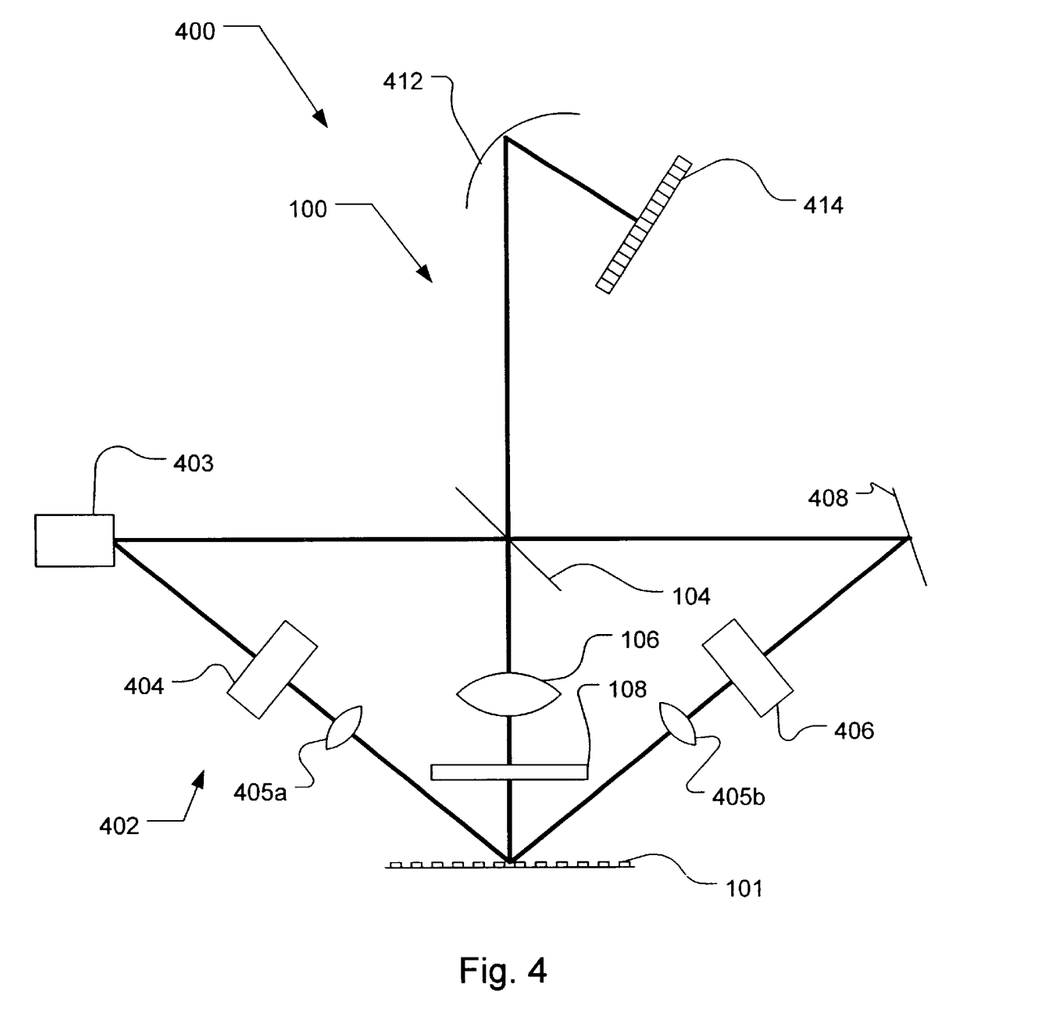
FIG. 4 shows another embodiment of a combined normal incidence spectroscopic polarized reflectometer and an oblique incidence polarimeter.

FIG. 4 shows another embodiment of a combined normal incidence spectroscopic polarimeter 100 and an oblique incidence polarimeter 402. The normal incidence spectroscopic polarimeter 100 operates as described above. As shown in FIG. 4, the two systems may share the same light source 403 and same spectrograph, which includes grating 412 and multichannel detector 414, similar to that described in the U.S. Patent Application entitled, "Discrete Polarization State Ellipsometer/Reflectometer Metrology System", by B. Johs, et al., Ser. No. 09/598,000, filed 06/19/2000, which is assigned to the assignee of the present disclosure and is incorporated herein by reference.

If desired, the two systems may share only one of the light source 403 or spectrograph, or as shown in FIG. 3, the two systems may have independent light sources and spectrographs. Similar to the embodiment shown in FIG. 3, the oblique incidence polarimeter 402 includes a PSG 404, and PSD 406 and lenses 405a and 405b. An optical element, such as a mirror 408 is used to redirect the reflected light beam toward beam splitter 104, which then redirects the beam towards the spectrograph. If desired other optical elements, such as fiber optic cables may be used in place of mirror 408.

The combination of the normal and oblique incidence spectroscopies provides a powerful technique in the characterization of complex structures, such as those shown in FIGS. 2B to 2C, including non-rectangular gratings and gratings over thin film stacks. Using the combined metrology system, such as that shown in FIG. 3, both normal incidence and oblique incidence data can be obtained. The experimental data collected at normal incidence (θ=0°) can be either the reflectance spectra [$R_{ET}(\theta=0°)$ and $R_{TM}(\theta=0°)$] or the ellipsometry angles ψ(θ=0°) and Δ(θ=0°), whereas at oblique incidence, the experimental data can be reflectance spectra [$R_{TE}(\theta=\phi)$ and $R_{TM}(\theta=\phi)$], or the ellipsometry angles ψ(θ=φ) and Δ(θ=φ), where 0<φ<90°. In one embodiment, the value of φ is 70°, but of course other angles may be used.

To obtain the useful parameters such as such as film thickness, side wall angles, linewidths, etc., an optical model is produced that is fit to the experimental data. As described before, an adequate optical model for critical dimension samples is RCWA, which is described in detail in Ser. No. 09/670,000 and Ser. No. 09/844,559.

To take advantage of the information gained by measuring both at oblique and normal incidence, the same physical model describing the sample structure is used to generate the optical models fitted to oblique and normal incidence sets of experimental data. The mathematical details to obtain the modeled spectra may vary for oblique incidence and normal incidence, i.e., the calculation of the modeled spectra uses the angle of incidence as a parameter. Furthermore, the speed of the normal incidence spectra calculation can be increased up by taking advantage of the symmetric spread of the diffraction orders, whereas at oblique incidence this symmetry is broken and therefore the calculation speed will be slower. Nevertheless, the basic theory (e.g., RCWA), and the basic optical model parameters (thickness, optical constants, side wall angles, etc.) must be the same for both data sets.

For example, the experimental data sets will be named $y_i$, where $y_i$ refers to any of the experimental data points measured at wavelength i, and $y_i$ can be any reflectance or ellipsometry data point, measured at either normal or oblique incidence. The fitting of the optical model generated, e.g., by RCWA, to the experimental data sets $y_i$ can be achieved by using Levenberg-Marquart regression analysis as described in W. H. Press, P. P. Flannery, S. A. Teukolsky, and W. T. Vetterling, "Numerical Recipes", Cambridge University Press (1986), which is incorporated by reference. The Levenberg-Marquart regression analysis is used to adjust the values of the fitting parameters in the optical model to minimize the mean-squared error (MSE), which is defined as:

$$MSE(\vec{x}) = \frac{1}{N-M} \sum_{i=1}^{N} \left( \frac{y_i - y_i(\vec{x})}{\sigma_i} \right)^2 ; \quad \text{eq. 1}$$

where N is the total number of data points (normal and oblique incidence); M is the total number of fitting parameters; $y_i$ is the experimental data point i (normal or oblique incidence reflectance, or ellipsometry angles (φ and Δ)); $y_i(\vec{x})$ is the ith calculated data point; $\vec{x}$ is the vector representing the variable fitting parameters [$\vec{x} = (x_1, x_2, \ldots, x_M)$]; and $\sigma_i$ is the standard deviation associated to the measured point $y_i$, which is the sum of systematic and statistical system errors, coming from calibration inaccuracies and signal noise, respectively. As can be seen from equation 1, the MSE will increase if $\sigma_i$ decreases. Therefore, data points with more error will weight less in the fitting result, since the Levenberg-Marquardt analysis is a procedure to minimize the MSE.

The contribution to the MSE can be very different for reflectance and ellipsometry data because reflectance values vary from 0 to 1 and ellipsometry angles vary from −180° to +180° for Δ, and from 0° to 90° to ψ. In order to have a similar range of values for all the quantities $y_i$ so that all the spectra are fit with same accuracy, usually the data points $y_i = \cos(\Delta)$ and $y_i = \tan(\psi)$ are used so that all the data points $y_i$ vary about the same range (−1 to 1). An other option is to fit Re(ρ) and Im(ρ), where ρ tanψ exp(iΔ).

The data analysis is performed by first, constructing an optical model for the sample under study. The optical model includes the substrate material, the number of films, the films configuration, i.e., grating structure or thin films, and the optical constants of each layer. The optical constants can be specified in a table as a function of wavelength or in a form of a dispersion model, such as, e.g., a Cauchy model. The optical model also includes initial guesses for variable parameters, such as thickness, linewidth, pitch, line profile for the films and gratings, and/or the parameters defining the dispersion model of the optical constants. The variable parameters are the parameters that are varied in order to fit the optical model to the experimental data. The Levenberg-Marquardt algorithm is then used to determine the values of the variable parameters that yield the calculated data that best matches the experimental values.

There is often a strong correlation between fitting parameters, i.e., a small change in a parameter $x_{j1}$ can result in a change of a calculated spectral value $y_i$ which may also be affected when adjusting another parameter $X_{j2}$. By simultaneously fitting normal and oblique incidence data collected from the same sample by the combined metrology system, the strong correlation of fitting parameters may advantageously be broken up. Breaking up the correlation of fitting parameters most commonly occurs in multilayered samples, since the optical path length differs for different angles of incidence. In addition, the typically strong correlation between thickness, sidewall angles and linewidths in diffraction grating structures can be broken when combining two different angles of incidence.

Unfortunately, the fitting speed of the combined normal and oblique incidence data is considerably reduced relative to a single angle incidence data, due to the time-consuming RCWA calculation. To increase the fitting speed in most applications, a hybrid methodology can be used that, when operating at fast mode, uses only normal incidence data. Then, the fitting parameters correlation matrix, whose elements quantitatively indicate how strongly correlated the fitting parameters are, can be tracked at real time. If the correlation becomes strong, the oblique incidence measurement can be used and the data analyzed as described above to break up the correlation and get more accurate parameters. Thus, for most instances, only normal incidence data is used to provide a relatively fast fitting speed, but where there is a strong correlation in fitting parameters, the additional incidence data is used to break up the correlation.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A metrology device for characterizing a grating structure on a sample, comprising:

a normal incidence polarimeter that focuses on said grating structure on said sample, said normal incidence polarimeter having a light source that produces a light beam, said light beam being normally incident on said sample, and a means for polarizing, said normally incident beam passing through said means for polarizing towards said sample and after reflecting off said sample; and an oblique incidence polarimeter that focuses on said grating structure on said sample.

2. The metrology device of claim 1, wherein said means for polarizing is a polarizer in the path of said normally incident light beam and wherein said normal incidence polarimeter further comprises a photometer that detects said normally incident light beam after interacting with said sample.

3. The metrology device of claim 2, wherein said oblique incidence polarimeter comprises:

a light source that produces a light beam, said light beam being obliquely incident on said sample;

a polarization state generator in the path of said obliquely incident light beam;

a polarization state detector in the path of said obliquely incident light beam after said obliquely incident light beam interacts with said sample; and a photometer that detects said obliquely incident light beam after interacting with said sample and said polarization sate detector.

4. The metrology device of claim 1, wherein said normal incidence polarimeter is a normal incidence spectroscopic polarimeter and said oblique incidence polarimeter is an oblique incidence spectroscopic polarimeter.

5. The metrology device of claim 3, wherein said normal incidence polarimeter and said oblique incidence polarimeter share the same light source.

6. The metrology device of claim 3, wherein said normal incidence polarimeter and said oblique incidence polarimeter share the same photometer.

7. The metrology device of claim 5, wherein said normal incidence polarimeter and said oblique incidence polarimeter share the same photometer.

8. A metrology apparatus comprising:

at least one radiation source that produces a beam directed to be normally incident at a location on a sample, and a beam directed to be obliquely incident at said location on said sample;

a polarizing element in the path of the normally incident beam, said normally incident beam passing through said polarizing element towards said sample and after reflecting off said sample;

a polarization state generator in the path of the obliquely incident beam, said obliquely incident beam passing through said polarization state generator toward said sample;

a polarization state detector in the path of said obliquely incident beam after said obliquely incident beam is reflected off said sample, said obliquely incident beam passing through said polarization state detector; and at least one photometer that detects said normally incident beam after being reflected off said sample and passing through said polarizing element and that detects said obliquely incident beam after being reflected off said sample and passing through said polarization state detector.

9. The apparatus of claim 8, wherein there are two radiation sources including a first source that produces said normally incident beam that passes through said polarizing element toward said sample, and a second source that produces said obliquely incident beam that passes through said polarization state generator.

10. The apparatus of claim 8, wherein said at least one radiation source is an at least one broadband radiation source.

11. The apparatus of claim 8, wherein there is one radiation source that produces said normally incident light beam and said obliquely incident light beam.

12. The apparatus of claim 8, wherein there are two photometers including a first photometer that detects said normally incident beam after being reflected off said sample and passing through said polarizing element and a second photometer that detects said obliquely incident beam after passing through said polarization state detector.

13. The apparatus of claim 8, wherein said at least one photometer is an at least one spectrophotometer.

14. The apparatus of claim 8, wherein there is one photometer that detects both said normally incident beam after being reflected off said sample and passing through said polarizing element and said obliquely incident beam after passing through said polarization state detector.

15. The apparatus of claim 8, further comprising a beam splitter in the path of said beam directed to be normally incident at a location on a sample, wherein said at least one radiation source produces said beam that is reflected by said beam splitter to be normally incident on said sample and wherein said normally incident beam at least partially passes through said beam splitter after being reflected off said sample and passing through said polarizing element.

16. The apparatus of claim 15, wherein said obliquely incident light beam is reflected by said beam splitter after passing through said polarization state detector and is directed towards said at least one photometer.

17. A method of characterizing a grating structure on a sample, the method comprising:

providing a polarized beam to be normally incident on said grating structure;

providing a polarized beam to be obliquely incident on said grating structure;

obtaining normal incidence data by detecting the normally incident beam after reflecting off said grating structure;

obtaining oblique incidence data by detecting the obliquely incident beam after reflecting off said grating structure;

generating calculated data using an optical model of said grating structure; and fitting said normal incidence data and said oblique incidence data to said calculated data to characterize said grating structure.

18. The method of claim 17, wherein said optical models for said normal incidence data and said oblique incidence data are generated based on the same physical model of said grating structure.

19. The method of claim 17, wherein said fitting said normal incidence data and said oblique incidence data to optical models is performed at the same time.

20. The method of claim 17, wherein said fitting said normal incidence data and said oblique incidence data to optical models is performed by fitting said normal incidence data to a first optical model and fitting said oblique incidence data to a second optical model when there is a strong correlation in fitting parameters in said first optical model.

* * * * *